United States Patent [19]
Cole

[11] Patent Number: 4,858,609
[45] Date of Patent: Aug. 22, 1989

[54] BRIGHT LIGHT MASK

[76] Inventor: Roger J. Cole, 12981 Via Esperia, Del Mar, Calif. 92014

[21] Appl. No.: 128,634

[22] Filed: Dec. 4, 1987

[51] Int. Cl.⁴ .............................................. A61N 5/06
[52] U.S. Cl. ..................................... 128/395; 600/26; 600/27
[58] Field of Search ............... 128/395, 396, 397, 398, 128/380; 600/26, 27

[56] References Cited
U.S. PATENT DOCUMENTS

| | | | |
|---|---|---|---|
| 4,315,502 | 2/1982 | Gorges | 600/27 |
| 4,665,926 | 5/1987 | Leuner et al. | 600/26 |

Primary Examiner—Leo P. Picard
Attorney, Agent, or Firm—Flehr, Hohbach, Test, Albritton & Herbert

[57] ABSTRACT

A bright light mask system for shining a high intensity light into a subject's eyes at preselected time periods to modify circadian rhyhyms. The system includes a mask adapted to be worn by the subject for covering the subject's eyes regardless of body position. The mask includes at least one light admitting aperture that is transparent to light energy. A light source is coupled to the aperture for generating and directing light into the subject's eyes. A light intensity of at least 2000 LUX of light having a wavelength in the range of 500 to 600 nanometers is delivered to each of the subject's eyes. A controller dictates the intensity of the light generated and the timing during which the light is on.

14 Claims, 3 Drawing Sheets

BRIGHT LIGHT MASK

BACKGROUND OF THE INVENTION

The present invention relates generally to an optical mask adapted to shine a sustained bright light into the wearer's eyes at selected times to modify circadian rhythms.

It has long been known that biological processes in most, if not all organisms vary rhythmically over time, and that the timing of these rhythms can be affected by exposure to light. Recent research suggests that the light must be very bright if it is to effectively modify biological rhythms in humans. Using carefully timed exposure to bright light, scientists have been able to change people's cycles of sleep and wakefulness, body temperature and hormonal secretion. Additionally, bright lights have been found useful in treating certain psychiatric disorders such as seasonal affective disorder and depression. It has also been suggested that light treatment may be useful to fight various sleep/wake problems such as jet lag and tiredness associated with shift work, and to improve nighttime vigilance and performance.

Bright lighting systems for modifying biological rhythms have traditionally consisted of large, bulky banks of fluorescent tubes or specialized bulbs. Such systems have several inherent drawbacks, including high energy consumption, high heat production and limited transportability. These restrict their usefulness outside of the laboratory environment, especially for mobile applications such as the treatment of jet lag.

Furthermore, some research has suggested that the critical time for bright light exposure for many therapeutic purposes is either late at night or early in the morning, when subjects are ordinarily asleep. Another advantage of bright light treatment during sleep time is that it does not take time away from preferred wakeful activities. With traditional lighting systems, subjects must be awake to receive treatment, for if they fall asleep they may shield their eyes or look away from the light source and thus receive insufficient exposure.

Therefore there is a need for a bright light source that is lightweight and transportable; develops sufficient light intensity to produce the desired biological effects; and reliably directs light into the user's eyes regardless of body position during sleep. Additionally, there is a need for a bright light source which may be turned on and off at preselected times during the day or night and is capable of turning on gradually so as not to disturb a wearer.

SUMMARY OF THE INVENTION

Accordingly, it is the primary objective of the present invention to provide a light weight and portable bright light source capable of generating a light intensity bright enough to modify human biological rhythms.

Another objective of the present invention is to provide a bright light source that includes a timer for turning on and off the light source at preselected times.

Another objective of the present invention is to provide a light source capable of varying the intensity of the light emitted.

Another objective of the present invention is to provide a light source that shines reliably into the eyes regardless of body position and without conscious effort on the part of the user.

Another object of the invention is to provide high intensity light to a subject's eyes without requiring high energy consumption.

To achieve the foregoing and other objects, and in accordance with the purpose of the present invention, a bright light mask system is provided for shining a high intensity light into a subject's eyes to modify circadian rhythms. The bright light mask includes a mask to be worn by the subject and adapted for covering a subject's eyes regardless of body position. The mask includes at least one light admitting aperture that is substantially transparent to light energy. A light means that is coupled to the light admitting aperture generates and delivers light through the light admitting aperture onto the subject's eyes. The light means includes a light source that light having a wavelength in the range of 500 to 600 nanometers, and delivers light having an intensity of at least 2000 LUX to the subject's eyes. A control means regulates the delivery of light to the subject's eyes.

Preferably the control means includes a timer means for selectively turning on and off the light source for at least 15 minute "on" cycles. Additionally, a dimming means controls the intensity of light delivered to the subject's eyes. Specifically, the dimming means is adapted to gradually increase the intensity of the bright light when the device is first turned on.

BRIEF DESCRIPTION OF THE DRAWINGS

The features of the present invention which are believed to be novel are set forth with particularly in the appended claims. The invention, together with further objects and advantages thereof, may best be understood by reference to the following description of the presently preferred embodiment, taken in conjunction with the accompanying drawings in which:

DETAILED DESCRIPTION OF ILLUSTRATIVE EMBODIMENTS

Figure 1:
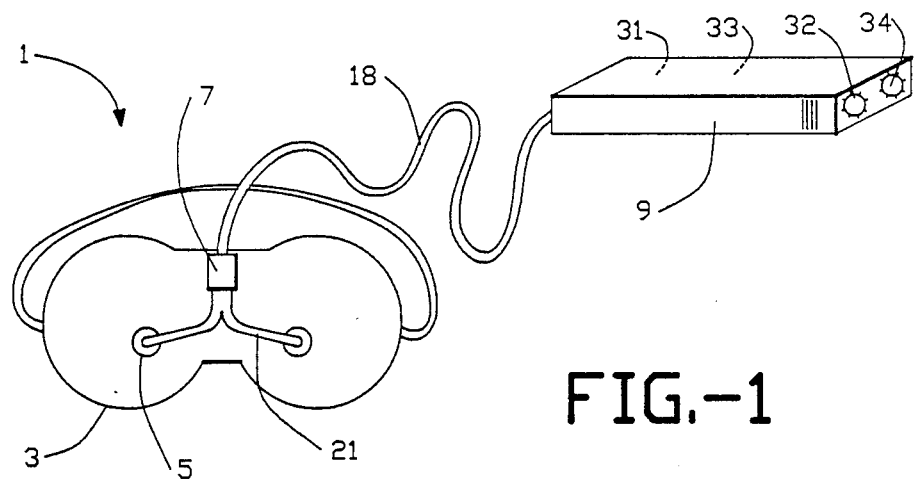
FIG. 1 is a front view of a bright light mask system 1 in accordance with the present invention.

As illustrated in the drawings, bright light mask system 1 of the present invention includes a standard sleep mask 3 having at least one light admitting aperture 5 therein, and a light means 7. The mask is adapted to cover the subject's eyes and its light admitting aperture 5 is transparent to light energy. The light means 7 generates light and directs the light through the light admitting aperture 5 in mask 3 and onto the subject's eyes. A controller 9 regulates the timing and intensity of the light source.

Figure 2:
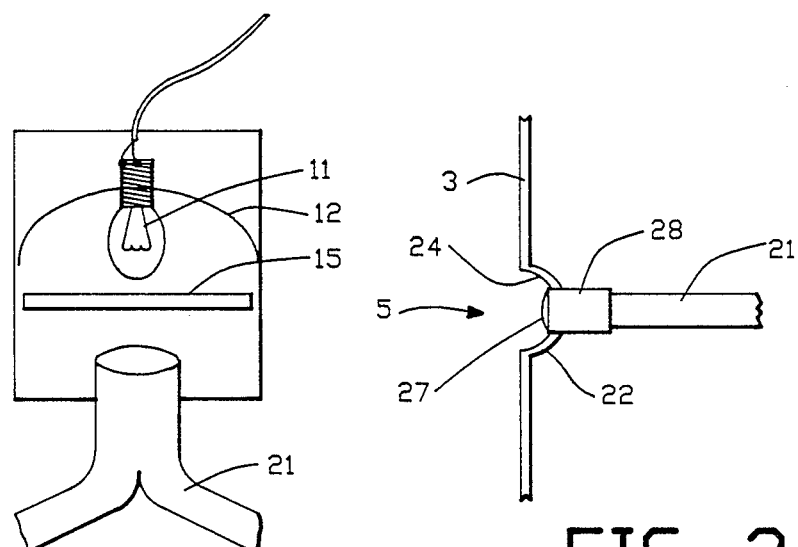
FIG. 2 is a schematic view of an embodiment of the light means appropriate for use in the bright light mask system shown in FIG. 1.
Figure 3:
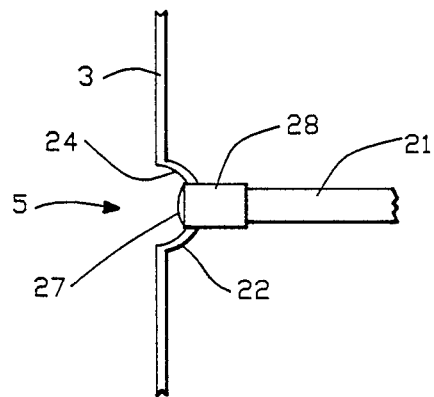
FIG. 3 is a side view detailing the fiber optic to mask connection of the bright light mask system shown in FIG. 1.

Referring initially to FIGS. 1-3, a presently preferred embodiment of the bright light mask system 1 will be described. The mask 3 is an ordinary sleeping mask worn to block out light at night when the user is asleep. A pair of openings 5 (which form the light emitting aperture) are cut into the mask directly over each eye. In order to modify circadian rhythms, it is necessary to deliver light that includes at least 2000 LUX at wavelengths in the range of 500-600 nm. The bright light generally must remain on for at least 15 minutes. In this embodiment, the light means 7 includes a single light source 11. A wide variety of conventional light sources may be used so long as they produce the required light. By way of example, as shown in FIG. 2, a standard incandescent flashlight bulb 11 complete with a curved reflector 12 for directing the light forward may be used as the light source. Filters 15 may optionally be used to control the type of light that enters the eyes. For example, it may be desirable to block either infra red or ultra violet rays depending upon the light source used. Additionally, in some applications it may be desirable to color filter the light. Heat generated by the light source is the major concern when incandescent bulbs are used. Therefore a heat reflective filter made of a material such as mylar will minimize heat delivery to the eyes while exposing them to bright light.

Referring also to FIG. 3, fiber optic cables 21 direct the filtered light from the light source 11 to the mask openings 5. Referring now to the junction between the mask and the fiber optic cables, spreader lens 27 is coupled to the distal end of each of the fiber optic cables 21 in order to disperse the light inside mask 3. The attachment between lens 27 and cable 21 is facilitated by a sleeve 28. A rigid holder 22 having a reflective concave inner surface 24 is disposed within the mask openings 5 and secured to the mask 3 by any conventional fastening means. Controller 9 functions both as a timer that is capable of turning the light source 11 on at various selectable time intervals and controlling the intensity of the light source. Electrical wires 18 join the light source to the controller. A more detailed description of the light source is provided below.

Figure 4:
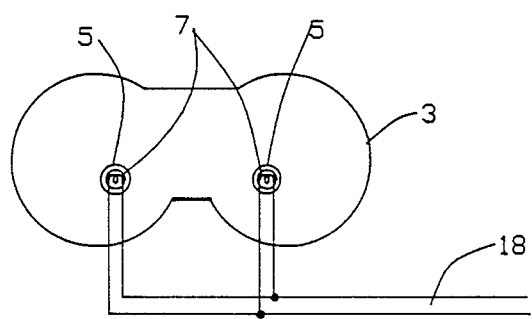
FIG. 4 is an alternative embodiment of the bright light mask system of the present invention.

An alternative embodiment of the light means 7 is illustrated in FIG. 4. In that embodiment, a pair of light sources in the form of miniature incandescent light bulbs 11 are placed directly in front of the openings 5 in mask 3. Filters 15 are particularly important in this embodiment to reduce the amount of heat reaching the eyes, since excess heating of the eyes could be damaging and the buffer inherently provided by fiber optic cables 21 is nonexistent. Alternatively, banks of high brightness green light emitting diodes could be used in place of the incandescent light bulb. The LED banks have the advantage of having lower power consumption and less heat dissipation. However, LED's of sufficient brightness are not readily available at economical prices.

In both of the embodiments described, a controller 9 controls the intensity of the light generated and the timing during which the light is on. It is frequently desirable to turn on the lights at preselected spaced intervals and particularly while the subject is asleep. Therefore, the controller 9 includes a timer 31 which may be set to turn on and off at any number of spaced time intervals. An intensity controller 33 controls the intensity of the light generated by light source 11. To avoid waking a sleeping subject, it is desirable to slowly increase the intensity of the light from OFF to full ON since sudden intense light changes will often awaken a sleeping subject. By way of example, ramping times in the vicinity of 16 minutes have been found to be appropriate.

The timer 31 includes a delay select switch 32 that allows the user to select a desired delay after which the light will turn on. Once the light has been turned on, intensity controller 33 incrementally increases the intensity of the light until the light is fully on. In essence, the controller functions as a variable voltage/current source which slowly increases the intensity of the light delivered to the subject's eyes. Duration select switch 34 controls the amount of time the light is on. By way of example, in the embodiment of the controller suitable for use with the present invention described below, the delay select switch 32 has hourly incremental delays of 0 to 15 hours while the duration select switch has incremental delays on the half hour between 0 and 7.5 hours. Also by way of example, the light gradually intensified from off to full power over a sixteen minute time period.

It should be appreciated that the present invention differs fundamentally from the prior art in that the intensity of the light source may be dramatically lower than the prior art while still delivering light bright enough to affect biological rhythms. This is due to the proximity of the light source to the subject's eyes, since as a light source is moved closer to an object being illuminated, the intensity of the light reaching the object is dramatically increased.

The bright light mask described will shine light of high enough intensity (at least 2,000 LUX) for a long enough duration (15 minutes to many hours) to produce a specific biological stimulus capable of rapidly and significantly shifting circadian rhythms and reducing the level of the hormone melatonin. Therefore, the mask applies energy to an organism to directly produce a physiological change. The bright light mask will not change biological rhythms unless the light is presented at the proper time of day. The mask described includes circuitry to control the on/off operation of the light.

A particular problem encountered by bright light sources is that the intensity of the light would be disturbing and possibly even damaging to the eyes if the light is turned on all at once. Therefore, the bright light mask described, is designed to turn on gradually.

Delivering bright light through a mask presents the special problem of delivering excessive heat to the eyes. In the initial embodiment described, this problem is overcome using fiberoptics to deliver the light, thereby removing the bulbs from the proximity of the wearer's eyes. Additionally, heat-reflective filters made of material such as Mylar provide another way to minimize heat delivery to the eyes while still exposing them to the bright light.

Figure 5:
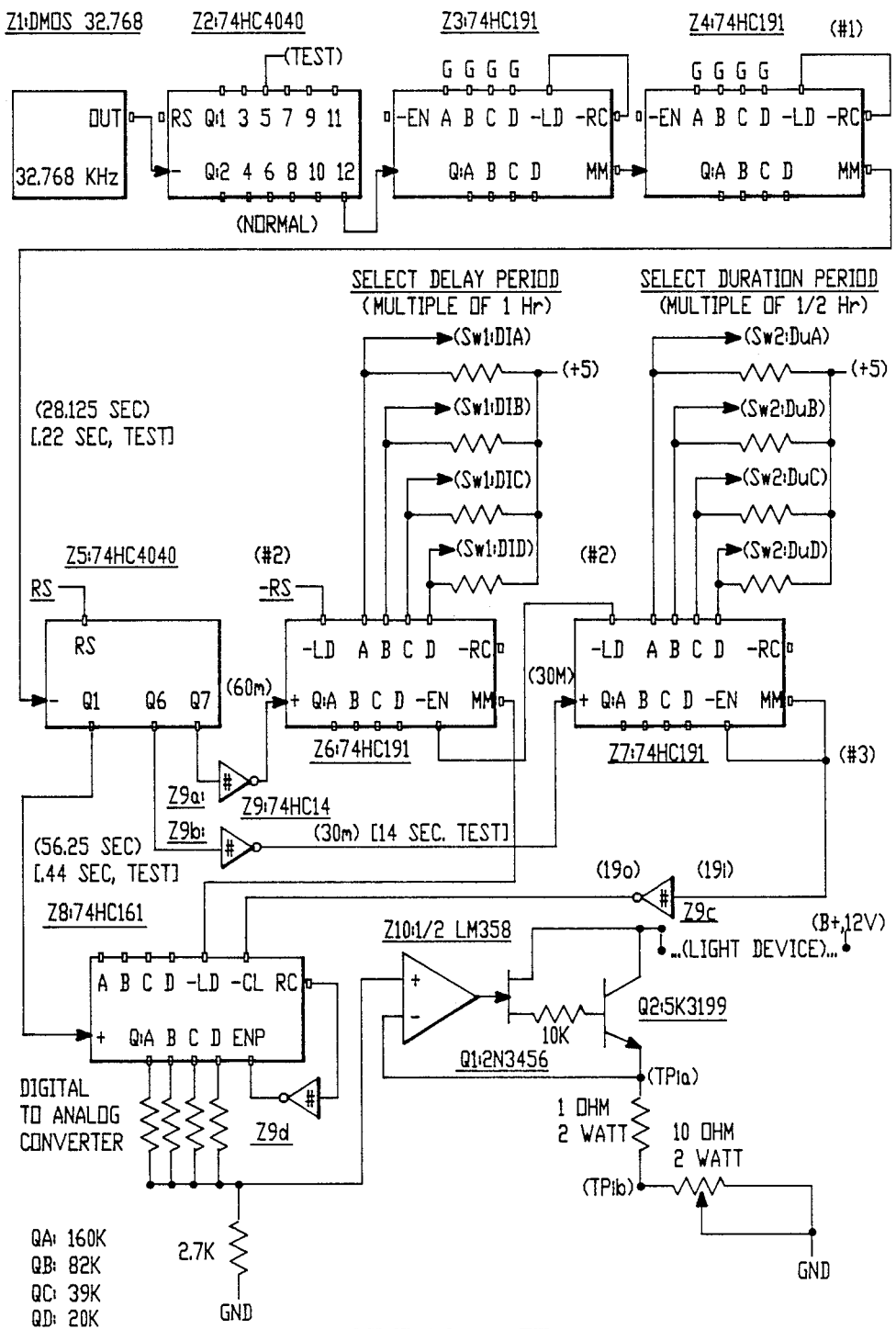
FIG. 5 is a circuit diagram of a controller suitable for use with the present invention.
Figure 6:
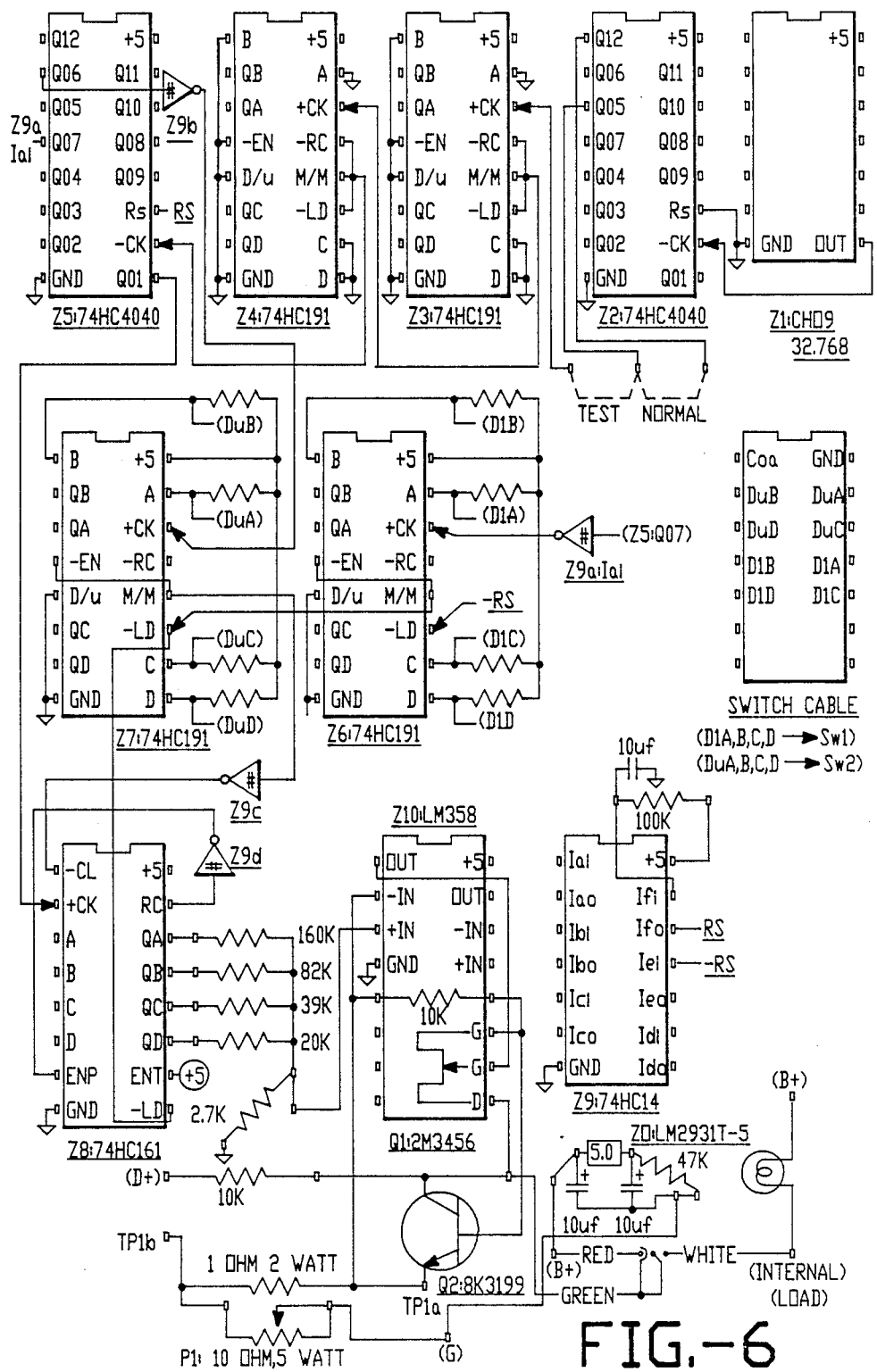
FIG. 6 is a suitable layout for the circuit diagram shown in FIG. 5.

One embodiment of the controller 9 suitable for use with the bright light mask is shown in FIGS. 5 and 6. As shown therein, the circuit is designed to run from an on-board 5.0 volt regulator, which requires an external source of power of 7 volts or more. The light device driven by this device may require any voltage. The external power supply may be as high as 30 volts, though something closer to 12 volts is recommended.

The light device and supply voltage should be arranged so that the supply voltage is as close as possible to 2-3 volts above the voltage required by the light device. This is to avoid wasting power—which must be dissipated by the power transistor (Q2). By way of example, an SK3199 medium power transistor, or equivalent, rated as 10 watts and 2 amperes, should be sufficient for most configurations. A higher rated power transistor might be required if the voltage source greatly exceeds the requirements of the lamps or devices.

The 5 watt potentiometer (P1) allows adjustment of the circuit for different light devices. The circuit is capable of driving currents from 1/10 to 1 amp, roughly. The actual current driven may be measured by connecting a voltmeter between two "tie-points": from TP1a to TP1b. These tie points are indicated on the circuit layout shown in FIG. 6.

There is an on-board lamp which is switched into the circuit when the light device is not connected into the 2.5 mm dc jack. This allows easy demonstration of the circuit functioning independent of external light devices.

A two-choice jumper connection on the circuit board may be used to allow normal operation, or "test-operation" at a much faster rate, to allow circuit demonstration and checkout. (The jumper connections are shown on the circuit layout.) The timing parameters for normal and test operation are listed below.

| Function | Normal Oper. | Test Oper. |
|---|---|---|
| Delay (0–15 steps) | 60 min | 28.13 sec |
| Duration (0–15) | 30 min | 14 sec |
| Turn-on ramp step | 56.25 sec | 0.44 sec |
| Turn-on ramp total | 15 min | 7.0 sec |

(As used herein and on the diagrams, signal levels are indicated in underlined boldface. Signals, such as EN, are considered to be active when high, unless the complement, such as −LD, is indicated.)

The timing signals originate from a 32.768 kilohertz crystal oscillator (Z1), which is divided (by Z2) by 4096 [or by 4096/128=32, in test mode], resulting in an 8 Hz signal [1024 Hz, test mode] output.

In Z3 and Z4 each ripple carry output (−RC, low) is connected to its own load input (−LD, load when low) so that each overflow of the counter will cause an automatic reload of the programmed inputs (A through D). The preset inputs are set at a value of 0, so that 15 counts are required for overflow. Thus, Z3 and Z4 act as modulo 15 counters.

(The two divisions by 15 are required to convert seconds into hours. The crystal oscillator is designed to produce exactly one second when divided by 2, 15 times. The subsequent divisions by 60, to convert to minutes and hours, require two divisions by 2 and a division by 15, each. The divisions are not actually done in that order—to save components. Actually, 12 divisions by 2 are done in Z2, followed by the two divisions by 15 in Z3 and Z4, followed by the remaining divisions by 2 for each timing signal in Z5.)

The signal leaving Z4 has a period of −28.125 seconds [0.22 s, test]. It is fed into Z5 to generate the ½-hour signal required for duration and the 1-hour signal required for delay, and the 56.25 seconds [0.44 s, test] fed into Z8 to generate the "turn-on" ramp.

When the power is first turned on, an R-C circuit provides a one second reset signal, high (RS) from Z9a, and low (−RS) from Z9b. These signals are used to reset counters Z5 (time division) and Z5 (delay). The effect of reset is passed on to counters Z7 and Z8 by Z6.

The reset signal (−RS) is connected to the load input (−LD) of Z6 so that when power is first turned on the preselected value of delay (Sw1, complemented value determined by D1a through D1d) is loaded into the counter; counting commences at the end of the 1 second reset. The output of Z6 (M/M) is connected to the load (−LD) inputs of Z7 and Z8. While Z6 is counting, its M/M output (which is low until overflow) keeps Z7 and Z8 at their preset load values, not allowing them to count. When Z6's delay count of is exhausted, its M/M output goes high, and both Z7 and Z8 are allowed to start counting.

Z8 counts at a fairly fast rate (56 sec steps), and when it overflows, its output (RC) (inverted by Z9d and connected to its own enable input (ENP)) causes inhibition of its own counting—it is "stuck" in the "on" state. (It is important that the low signal on ENP disables the clocking (counting), but not the output—since counting is disabled, the output will not change, and Z8 stays at its maximum count). The four (binary) outputs of Z8 are connected to resistors which are "weighted" by powers of two, so that the combined outputs produce an analog voltage which is proportional to the binary number reflected in the counter. The 2.7K resistor (to ground was selected so that the maximum voltage 9Z8 at maximum count would be 1 volt. The output of this digital-to-analog converter is connected to the lamp drive circuitry described below.

At the same time that Z8 starts its "turn-on" count, the much slower duration counter Z7 also begins its count (of half hour intervals). When its count is completed, its output (M/M, inverted by Z9c and connected to the clear input, −CL, of Z8) clears Z8 (which was "stuck" in the on-state at the end of its ramp). Since the M/M output of Z7 is connected to its own enable input (−EN), it remains in its on-state—keeping Z8 cleared (lamp off) until power is turned off and then on again.

Although only a few embodiments of the present invention have been described herein, it should be apparent to those skilled in the art that the present invention may be embodied in many other specific forms without departing from the spirit or scope of the present invention. Particularly a wide variety of light sources, mask arrangements, filters and controllers could be fabricated to accomplish the goals of the present invention. Additionally, it should be appreciated that the bright light mask may be used to modify biological rhythms of a wide variety of subjects, in addition to humans. Thus, it is contemplated that suitable subjects would include, for example, laboratory monkeys, race horses, or animals being transported long distances. Therefore, the present examples and embodiments are to be considered as illustrative and not restrictive, and the invention is not to be limited to the details given herein, but may be modified within the scope of the appended claims.

I claim:

1. A bright light mask for shining a high intensity light into a subject's eyes to modify biological rhythms, the bright light mask comprising:

a mask adapted to be worn by the subject for covering the subject's eyes regardless of body position, the mask having at least one light admitting aperture that is transparent to visible light energy;

lighting means coupled to the mask for generating bright light and delivering cool light at selected intensity and frequencies sufficient to modify biological rhythms, the light means including a light means for generating bright light; and control means for regulating the delivery of light to the subject's eyes, the control means including timer means for turning the light source on and off at variable preselected times, and dimmer means for varying the intensity of the light delivered to the subject's eyes, wherein said dimmer means is arranged such that each time the timer means turns the light source on, the dimmer means gradually increases the intensity of the light delivered to the subject's eyes.

2. A bright light mask as recited in claim 1 wherein said light means delivers light onto the subject's eyes having an intensity of at least 2000 LUX within the wavelength range of 500 to 600 nanometers.

3. A bright light mask as recited in claim 1 wherein the light admitting aperture includes a pair of spaced apart mask openings, each mask opening being associated with a particular one of the subject's eyes.

4. A bright light mask as recited in claim 1 wherein said light source includes a pair of light bulbs, each light bulb being associated with a particular one of the mask opening.

5. A bright light source as recited in claim 4 wherein said light means further includes a spreader lens for directing the light emanating from said fiber optic cable towards the subjects eyes.

6. A bright light mask as recited in claim 1 wherein said light means further includes fiber optic cable for transmitting light generated by said light source to said mask openings and directing the light onto the subjects eyes.

7. A bright light mask for shining a high intensity light into a subject's eyes to modify biological rhythms, the bright light mask comprising:
   a mask adapted to be worn by the subject for covering the subject's eyes regardless of body position, the mask having at least one light admitting aperture that is substantially transparent to visible light energy;
   a bright light source coupled to the mask for generating light having an intensity of at least 2000 LUX within the wavelength range of 500 to 600 nanometers;
   delivery means suitable for delivering the bright light from the light source to the subject's eyes, wherein the delivery means delivers cool light to the subject's eyes;
   control means for regulating the delivery of light to the subject's eyes, the control means including timer means for turning the light source on and off at variable preselected times; and dimmer means for varying the intensity of the light delivered to the subject's eyes, wherein said dimmer means is arranged such that each time the timer means turns the light source on, the dimmer means gradually increases the intensity of the light delivered to the subject's eyes.

8. A bright light mask as recited in claim 7 wherein said delivery means includes an optical filter suitable for blocking infrared radiation.

9. A bright light mask as recited in claim 8 wherein said delivery means includes an optical filter suitable for blocking ultraviolet radiation.

10. A bright light mask as recited in claim 7 wherein said delivery means includes a fiber optic cable.

11. A bright light mask as recited in claim 7 wherein the dimmer means gradually increases the intensity of the light generated by the light source over a period greater than one minute.

12. A method of modifying the biological rhythms of a subject comprising the steps of:
   selectively directing a cool bright light into the subject's eyes, the light having an intensity of at least 2000 LUX at wavelengths in the range of 500 to 600 nanometers; and
   gradually increasing the intensity of the light delivered when the light is first turned on over a period of at least one minute.

13. A method as recited in claim 12 wherein light having an intensity of at least 2000 LUX is delivered to the subject's eyes for a period of at least 15 minutes.

14. A method of modifying the biological rhythms of a subject comprising the steps of:
   selectively directing a bright light into the subject's eyes, the light having an intensity large enough to modify the subject's circadian rhythms and being delivered through a mask worn by the subject; and
   gradually increasing the intensity of the light delivered to the subject's eyes over a period of at least one minute when the light is first turned on.

* * * * *

UNITED STATES PATENT AND TRADEMARK OFFICE
CERTIFICATE OF CORRECTION

PATENT NO. : 4,858,609

DATED : August 22, 1989

INVENTOR(S) : Roger Cole

It is certified that error appears in the above-identified patent and that said Letters Patent is hereby corrected as shown below:

Title page, after "Roger J. Cole", delete [12981] and insert --12759--.

Title page, after "Via", delete [Esperia] and insert --Felino--.

Column 2, line 16, after "that", insert --generates--.

Column 2, line 68, after "light", delete [emitting] and insert --admitting--.

Column 6, line 2, after "count", delete [of].

Column 6, line 16, after "(to ground", insert --)--.

Column 6, line 60, after "intensit", delete [y] and insert --ies--.

Column 7, line 14, after "said light", delete [source] and insert --means--.

Column 7, line 16, after "opening", insert --s--.

Column 7, line 17, after "claim", delete [4] and insert --6--.

UNITED STATES PATENT AND TRADEMARK OFFICE
CERTIFICATE OF CORRECTION

PATENT NO. : 4,858,609

DATED : August 22, 1989

INVENTOR(S) : Roger Cole

It is certified that error appears in the above-identified patent and that said Letters Patent is hereby corrected as shown below:

Column 7, line 23, delete [source] and insert --means--.

Signed and Sealed this

Twenty-eighth Day of July, 1992

Attest:

DOUGLAS B. COMER

Attesting Officer

Acting Commissioner of Patents and Trademarks